United States Patent [19]

Tanaka

[11] Patent Number: 5,266,461
[45] Date of Patent: Nov. 30, 1993

[54] METHOD FOR DETERMINING (1-3)-β-D-GLUCAN

[75] Inventor: Shigenori Tanaka, Tokyo, Japan

[73] Assignee: Seikagaku Corporation, Tokyo, Japan

[21] Appl. No.: 835,956

[22] PCT Filed: Jun. 21, 1991

[86] PCT No.: PCT/JP91/00845
§ 371 Date: Feb. 20, 1992
§ 102(e) Date: Feb. 20, 1992

[87] PCT Pub. No.: WO91/19981
PCT Pub. Date: Dec. 26, 1991

[30] Foreign Application Priority Data

Jun. 21, 1990 [JP] Japan ................... 2-161281

[51] Int. Cl.$^5$ ............................................. C12Q 1/00
[52] U.S. Cl. ................................. 435/7.21; 435/7.32; 435/7.37
[58] Field of Search .................. 435/7.21, 7.32, 7.37

[56] References Cited

PUBLICATIONS

Wragoh et al.–Chem. Abst. vol. 109 (1988) p. 185023v.
Uragoh et al, *J of Histochem. and Cytochem.*, 36(10):1275-1283.

Primary Examiner—Sam Rosen
Attorney, Agent, or Firm—Sughrue, Mion, Zinn, Macpeak & Seas

[57] ABSTRACT

The present invention provides a reagent for determining (1→3)-β-D-glucan comprising limulus amebocyte lysate and an antibody to an endotoxin-sensitive factor, or comprising endotoxin-sensitive factor-free lysate, which enables highly sensitive determination of mycotic (1→3)-β-D-glucan present in biological samples such as blood, urine and cerebrospinal fluid without any interference of endotoxin. Thus, deep mycosis difficult to detect can be rapidly diagnosed with a good reproducibility. Accordingly, the present invention greatly contributes to the clinical diagnosis. specifically the assay is aided by the removal of intefering endotoxin sentitive factor.

3 Claims, 4 Drawing Sheets

METHOD FOR DETERMINING (1-3)-β-D-GLUCAN

TECHNICAL FIELD

The present invention relates to a reagent for determining (1→3)-β-D-glucan using limulus amebocyte lysate.

TECHNICAL BACKGROUND

A method of determining endotoxin using limulus amebocyte lysate (hereinafter abbreviated as lysate) is known. This method utilizes the coagulation of the lysate with a trace amount of endotoxin. The subsequent biochemical analysis reveals that the coagulation reaction is caused by a stepwise activation of several coagulation factors (Takanori Nakamura et al., Japanese Journal of Bacteriology, 38, 781–803 (1983)).

That is, as shown in FIG. 1, when endotoxin is added to the lysate, factor C (endotoxin-sensitive factor, molecular weight: 123,000) is activated to form an activated factor C. This activated factor C restrictedly hydrolyzes factor B (molecular weight 64,000), whereby the factor B is activated to form an activated factor B, which activates a proclotting enzyme (molecular weight: 54,000) to change into a clotting enzyme. The clotting enzyme restrictedly hydrolyzes specific sites Of $Arg^{18}$-$Thr^{19}$ and $Arg^{46}$-$Gly^{47}$ of coagulogen (coagulating protein, molecular weight: 19,723) to liberate a peptide C. The coagulogen is converted to coagulin, which causes coagulation (gelation). It is known that endotoxin can be quantitatively determined by the method of Iwanaga et al., (Haemostasis, 7, 183–188 (1978)) in which the lysate is used in combination with a synthetic peptide having an amino acid sequence corresponding to that of the hydrolyzed site of this coagulogen, i.e., the chromogenic substrate Boc-Leu-Gly-Arg-p-nitroanilide (pNA) or fluorogenic substrate Boc-Leu-Gly-Arg-4-methylcoumaryl-7-amide. This determination method utilizes a series of a reaction in which endotoxin triggers of a cascade mechanism for subsequently activating plural coagulation factors (which are all serine protease precursors) to finally form a coagulin gel. When (1→3)-β-D-glucan is added to the lysate, factor G is activated to an activated factor G, which functions to convert the proclotting enzyme to the clotting enzyme as shown in FIG. 1. Then, as in the case of endotoxin, the clotting enzyme functions to convert coagulogen to a coagulin which forms a gel and hydrolyzes a synthetic substrate (Morita et al., FEBS Lett., 129, 318–321 (1981)).

The substances which react with factor G include (1→3)-β-D-glucan, krestin, lentinan, and substances contained in the rinses from cellulosic hemodialyzer and in the blood contacted with the dialyzer. These substances are confirmed to exhibit no pyrogenesity by the rabbit pyrogenic test.

On the other hand, (1→3)-β-D-glucan is known as a polysaccharide for constituting a mycotic cell wall. It is feasible to detect the presence of mycetes within the body by determining (1→3)-β-D-glucan in blood, and therefore, a method for accurate and reproducible determination of (1→3)-β-D-glucan without any interference of endotoxin is desired, particularly, in the field of clinical diagnosis.

Further, it is reported that seventeen anti-factor C monoclonal antibodies are prepared and these antibodies are examined for identification of their epitope regions and an effect for the activation of factor C (Yoshiki Miura et al., Biochemistry, 61, No. 9, 834 "Identification of monoclonal antibodies to lp-Ajo6 lipopolysaccharide-sensitive serine protease precursor (factor C) and application thereof to analysis of activation mechanism", Sep. 25, 1989, published by The Japanese Biochemical Society).

Further, a method of determining (1→3)-β-D-glucan using factor G in the lysate has been reported (Obayashi et al., Clin. Chim. Acta. 149, 55–65 (1985)). This method comprises fractionating the lysate by gel filtration or affinity chromatography using a carrier having heparin or dextran sulfate fixed thereon to remove endotoxin-sensitive factor C and recombining only factor G and proclotting enzyme. Thus, the method requires extremely complicated operation.

DISCLOSURE OF THE INVENTION

The present invention relates to a reagent for determining (1→3)-β-D-glucan using an antibody to an endotoxin-sensitive factor and utilizing a reaction with factor G in the lysate without the influence of endotoxin-sensitive factor C.

According to the present invention, the reagent for assaying (1→3)-β-D-glucan comprises (1) the lysate and the antibody to endotoxin-sensitive factor, or (2) the lysate free from endotoxin-sensitive factor, obtained by contacting the lysate with a carrier having an antibody to endotoxin-sensitive factor fixed thereon.

The endotoxin-sensitive factors include, as described above, factor C which is activated with endotoxin and factor B which is activated with the activated factor C. Thus, in order to specifically determine (1→3)-β-D-glucan without being affected by endotoxin, the influence of these factors C and B contained in the lysate must be obviated. Therefore, in accordance with the present invention, an antibody against to the factor C or the mixed factors C and B (hereinafter, factor CB) is used together with the lysate. Alternatively, factor C-free lysate obtained by using an anti-factor C antibody-fixed carrier can be used.

The lysate used in the present invention is obtained by collecting hemolymph from horseshoe crab such as *Limulus polyphemus* in America, *Tachypleus gigas* in Thailand and Malaysia, *Tachypleus tridentatus* in Japan and *Carcinoscorpius rotundicauda* in Thailand and Malaysia, then fracturing blood cells, followed by separating a lysate component. Preferably, the resulting lysate is divided into small portions and stored at −40° C. or below and is defreezed upon use.

For producing the antibody to factor C from the resulting lysate, factor C which is used as an antigen should firstly be purified, for example, by contacting the lysate with the product obtained by fixing dextran sulfate, heparin or the like on an appropriate carrier such as agarose, Sepharose (trade name of the product available from Pharmacia) or the crosslinked product thereof, then collecting the fraction containing factor C or CB. The contacting method includes, for example, a method of contacting the lysate with the above-described fixation product in a solution, and a method using column chromatography.

The antibody to an endotoxin-sensitive factor is produced using the purified endotoxin-sensitive factor C or CB as the antigen(s). The resulting products are polyclonal antibody and monoclonal antibody to these antigens.

The polyclonal antibody used in the present invention can be prepared by administering the antigens to animals to be immunized such as rabbits and goats to thereby obtain an antibody, and, preferably, further purifying the thus-obtained antibody. Preferably, an adjuvant is administered to the animals to be immunized together with the antigens since it desirably activates the antibody-producing cells.

The monoclonal antibody used in the present invention can be prepared in the following manner. After intraperitoneally administering the antigen to mice or rats, a spleen or the like is taken out, then, cells obtained from the spleen or the like and myeloma cells which are tumor cell strains are subjected to cell fusion to obtain hybridoma. The thus-obtained hybridoma is continuously proliferated in a test tube, the screening is carried out for selection of the cell strain which continuously produces a specific antibody to the above-described antigen, and then, the resulting strain is cultured in vitro or in vivo such as an abdominal cavity of mice to obtain monoclonal antibody in a large quantity. Usable as the cells used in the cell-fusion, in addition to spleen cells are lymphonode cells, lymph cells in peripheral blood and the like. The myeloma cell strain is desirably one derived from the same kind cell strain as compared with one derived from different kind of cell strain, since a stable antibody-producing hybridoma can be obtained.

The thus-obtained polyclonal antibody and monoclonal antibody can be purified by salting-out with neutral salts such as sodium sulfate and ammonium sulfates, a low temperature alcohol precipitation and a selective fractional precipitation with polyethylene glycol or by an isoelectric point, electrophoresis, chromatography using ion-exchangers such as DEAE- and CM-derivatives or adsorbents such as protein A and hydroxyapatite, gel filtration and ultracentrifugation.

In the case of assaying $(1\rightarrow3)$-$\beta$-D-glucan using the above-described reagent (1), a solution containing the lysate, $(1\rightarrow3)$-$\beta$-D-glucan and the antibody can be prepared, for example, by: adding a solution of the antibody to a solution prepared by dissolving a freeze-dried lysate in distilled water or an appropriate buffer; previously adding a necessary amount of the antibody solution to the lysate, followed by freeze-drying and dissolving the freeze-dried reagent in distilled water or an appropriate buffer; adding the antibody solution to a solution prepared by dissolving a freeze-dried lysate and a freeze-dried synthetic substrate in an appropriate buffer, etc.; previously adding a necessary amount of the antibody solution to a mixture of the lysate and a synthetic substrate, followed by freeze-drying, and dissolving the freeze-dried reagent in a distilled water or an appropriate buffer; and adding a necessary amount of the antibody solution to a sample solution.

The factor C-free lysate obtained by contacting the lysate with a carrier having the antibody fixed thereon used in the above-described reagent (2) can be prepared by contacting the lysate with the carrier and then removing the carrier by centrifugation, filtration, or by applying the lysate to a column packed with the carrier and collecting the passed fraction.

The antibody-fixed carrier can be obtained by covalently binding an amino group of the antibody to a hydroxyl group of an appropriate carrier such as Cellulofine (trade name of the product available from Seikagaku Corporation) or Sepharose. Examples of the carrier include cellulose, agarose, polyacrylamide, dextran, porous silica beads, etc.

The antibody can be immobilized on these carriers by introducing an active group to a carrier and binding the antibody thereto. For example, epoxy groups are introduced to a carrier, followed by formylation, and the antibody is bound thereto.

A pH in the case of contacting the lysate with an immobilized carrier is not restricted as far as coagulation factors involved in a coagulation pathway initiated by factor G in the lysate, and by $(1\rightarrow3)$-$\beta$-D-glucan and factor G are not inactivated. However, it preferably ranges 6 to 9. A temperature in this case is not also restricted as far as the coagulation factors are not inactivated. However, it may range 0° to 45° C., preferably 0° to 10° C.

Biological samples to be assayed for $(1\rightarrow3)$-$\beta$-D-glucan include, in addition to blood, plasma, serum and endogenous or exogenous exudate and excretion such as cerebrospinal fluid, ascites, articular fluid, pleuritic fluid and urine. When plasma is used as a sample, it is required to separate a fraction containing $(1\rightarrow3)$-$\beta$-D-glucan by adding an anti-coagulant such as heparin, EDTA and citric acid.

Using the reagent according to the present invention, $(1\rightarrow3)$-$\beta$-D-glucan can be assayed for example, by: a method comprising adding the above-described chromogenic synthetic substrate or a fluorogenic substrate to a reaction mixture and determining an amidolytic activity of clotting enzyme; a gelation method in which the presence or absence of a gel formed by a coagulation reaction is observed by naked eyes; a turbidimetric method in which turbidity according to coagulation is measured with an appropriate optical system; a turbidimetric kinetic assay in which the time necessary for reaching a predetermined turbidity is measured with an appropriate optical system; and a method of using a quartz chemical analyzer to determine the change in a viscosity according to coagulation in terms of a change in resonant frequency.

The reagent for assaying $(1\rightarrow3)$-$\beta$-D-glucan of the present invention containing an antibody to factor C is characterized by an ability to specifically bind to factor C and a neutralization effect against factor C even in a small quantity. Secondly, it is characterized by containing no protease inhibitor such as antitrypsin and antithrombin III known as limlus reaction inhibitors and therefore the lysate does not lose any factor G activity.

BEST MODE OF PRACTICE THE INVENTION

The present invention is further illustrated by way of the following Examples, but, by no means limited thereto.

EXAMPLE 1

Production of polyclonal antibody to factors B and C

One liter of limulus hemolymph was centrifuged at 1,500 rpm for 10 minutes at 4° C. or below. To about 50 g of the resulting precipitate (amebocyte) was added 250 ml of 0.02 M Tris-HCl buffer (pH 8.0), and the mixture was homogeneously fractured by means of the homogenizer (Polytron R PT10 (trade mark), manufactured by Kinematica Co.) followed by extraction. The extract was centrifuged at 10,000 rpm for 30 minutes by means of the cooling-centrifuge (Tomy Seiko Co. RD-20III). The resulting precipitate was extracted twice with 150 ml of the above-described buffer to finally obtain 550 ml of the lysate.

Figure 1:
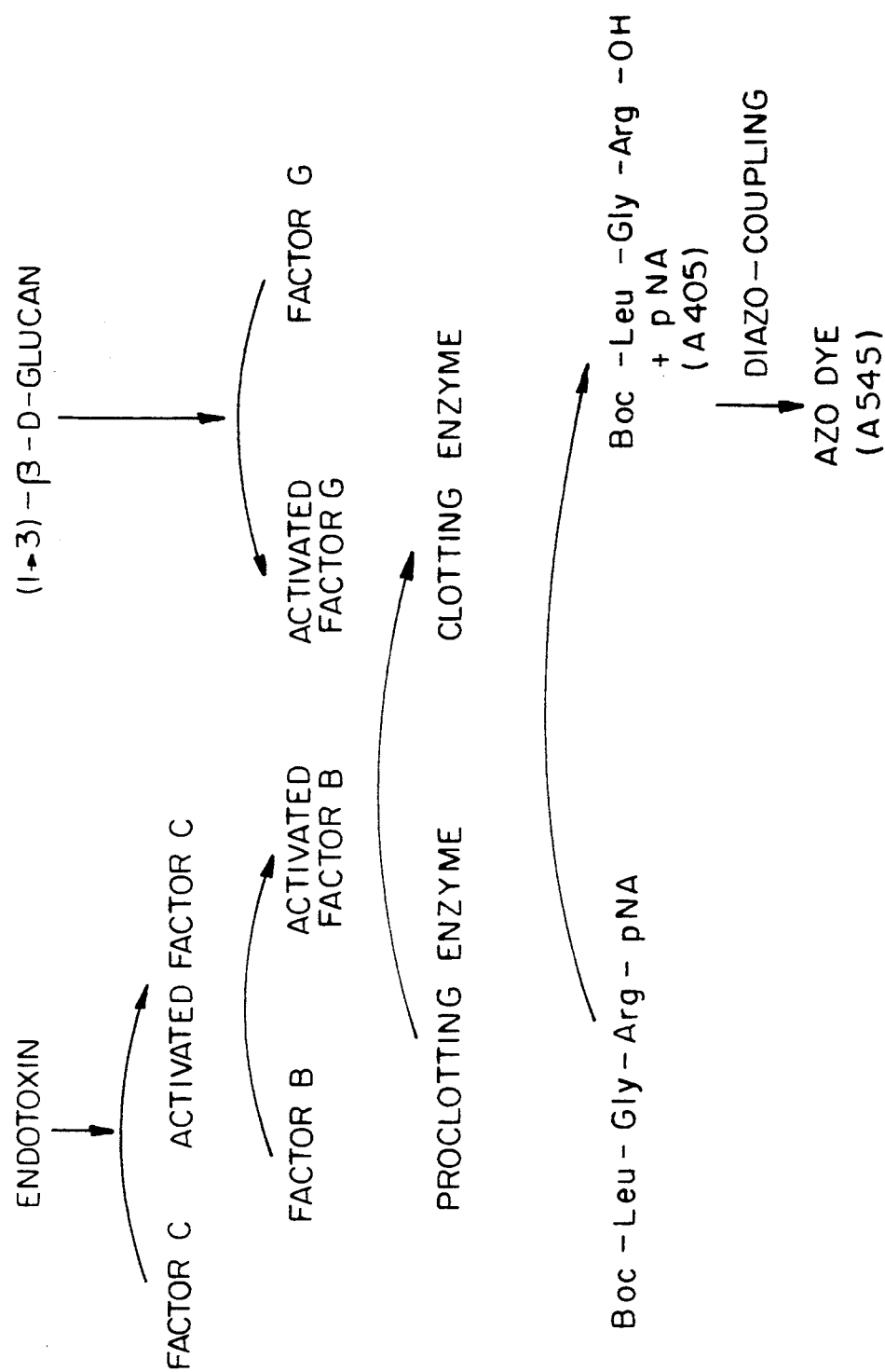
FIG. 1 shows a cascade mechanism of limulus blood coagulation.

The total amount of the obtained lysate was applied to a Sepharose CL-6B column having dextran sulfate fixed thereon (5×23 cm, equilibrated with 0.05M NaCl-containing 0.02M Tris-HCl buffer (pH 8.0)). The fraction obtained by elution with 0.45M NaCl-containing 0.02M Tris-HCl buffer (pH 8.0), i.e., fraction BC comprising factors B and C shown in FIG. 1 was evaluated for its activity according to the method of Obayashi et al (Clin. Chem. Acta., 149, 55–65 (1985)) as described below. Successively, after 40 ml of the same was concentrated to 10 ml under a reduced pressure, 0.23 g of EDTA-4Na was added to the concentrate for inhibiting the activation of factors C and B.

To 1.0 ml of the resulting mixture was added the same amount of Freund's complete adjuvant (trade name of the product available from Iatron). 0.3 ml, 0.3 ml and 0.4 ml of the same were subcutaneously injected (sensitization), respectively, into the back, the hip and the side of the abdomen of a rabbit (JW ♂ 2.5 kg). The sensitization was effected 5 times in all at the rate of once per two weeks. One week after the final sensitization, the increase in an antibody titer was confirmed by the double immunodiffusion, and the cervical vein of the rabbit was cut to collect all blood. After allowing the obtained blood to stand at room temperature for 1 hour and thereafter overnight at 4° C., the centrifugation was effected at 2,000 rpm for 5 minutes. 55 ml of the resulting serum was heat treated at 56° C. for 30 minutes to inactivate the same, followed by the addition of 0.06 g of sodium azide (0.1% (w/v)) as a preservative. To 48 ml of the resulting serum was added 48 ml of a 34% (w/v) Na$_2$SO$_4$ solution and the formed precipitate was separated by centrifugation at 10,000 rpm for 30 minutes. The resulting precipitate was washed twice with a 17% (w/v) Na$_2$SO$_4$ solution and dissolved in 50 ml of 0.1 M Tris-HCl buffer (pH 8.0). Into the solution, 7.5 g of solid Na$_2$SO$_4$ was dissolved with stirring, and the formed precipitate was dissolved in the above-described Tris-HCl buffers. This precipitation procedure was repeated three times at a Na$_2$SO$_4$ concentration of 7.5 g/50 ml. The final precipitate was dissolved in the above-described buffer, and the resulting solution was passed through the Cellulofine GH-20m (trade name of the product available from Seikagaku Corporation) column (2.8×90 cm, eluted with 0.05M NH$_4$HCO$_3$) The eluate was desalted followed by freeze-drying to obtain the IgG solution of rabbit anti-fraction BC serum.

Determination of activities of factors C and B

To 0.1 ml of 0.2M tris-HCl buffer (pH 8.0, containing 0.013 M MgCl$_2$) were added 30 μl of endotoxin (600 ng/ml) derived from *E. coli* 0111:B4 and further 50 μl of each fraction followed by heating at 37° C. for 15 minutes. Then, 20 μl of 0.005M N-tertiary butoxycarbonyl (Boc)-Leu-Gly-Arg-pNA (p-nitroanilide) and 50 μl of proclotting enzyme were added thereto to effect a reaction at 37° C. After confirming a color development, the reaction was stopped by adding 0.8 ml of 0.6M acetic acid and the absorbance at 405 nm was measured.

EXAMPLE 2

Production of polyclonal antibody to purified factor C 1.2 liter of limulus hemolymph was centrifuged at 1,500 rpm for 10 minutes at 4° C. or below. To about 53 g of the resulting precipitate (amebocyte) was added 250 ml of 0.02M Tris-HCl buffer (pH 8.0, containing 0.05M NaCl, 0.001M benzamidin, 0.001M EDTA-4Na). The mixture was fractured and was extracted, followed by centrifugation at 10,000 rpm for 30 minutes, as in Example 1. The resulting precipitate was extracted twice with 200 ml of the above-described buffer to finally obtain 640 ml of the lysate.

The total amount of the obtained lysate was applied to a Sepharose CL-6B column having dextran sulfate fixed thereon (5×23.5 cm, equilibrated with 0.05M NaCl-containing 0.02M Tris-HCl buffer, pH 8.0) and the fraction obtained by elution with 0.5M NaCl-containing 0.02M Tris-HCl buffer (pH 8.0) (factors B and C, activities of which were determined according to the method described in Nakamura et al., Eur. J. Biochem., 154, 511–521 (1986) as mentioned below) was concentrated by ultrafiltration (Dia Flow Membrane PM10, Amicon). Then, the resulting concentrate was subjected to gel filtration using a Sepharose CL-6B (manufactured by Pharmacia) column (4.0×129 cm, equilibrated with 0.02M sodium acetate buffer containing 0.1 M NaCl, pH 5.0) and ion exchange chromatography using CM-Sepharose CL-6B (manufactured by Pharmacia) column (2.0×25 cm, equilibrated with the above-described buffer, gradient-elution with 0.1M to 0.35M NaCl) to obtain 15.5 mg of the purified factor C. A purity of the purified factor C was examined with SDS polyacrylamide electrophoresis. As a result, one clear band was observed under a non-reduced condition, while two bands were observed under a reduced condition. Thus, it was apparent that the C factor is a highly purified product consisting of two polypeptide chains combined with a s—s bond with each other.

Determination of activity of factor C

To 20 μl of 1M Tris-HCl buffer (pH 8.0, containing 0.05M MgCl$_2$) were added 4 μl of endotoxin (10 μg/ml) derived from E. coli 0111:B4 and further, 10 to 20 μl of each fraction to make the total amount of 200 μl. After heating at 37° C. for 10 minutes, 50 μl of 0.002M Boc-Val-Pro-Arg-pNA was added thereto and the mixture was further heated at 37° C. for 7 minutes. 0.8 ml of 0.6M acetic acid was added to the mixture to stop the reaction. Then, the absorbance at 405 nm was measured.

Determination of activity of factor B

To 20 μl of 1M Tris-HCl buffer (pH 8.0, containing 0.05M MgCl$_2$) was added 10 μl of an activated factor C solution (prepared by adding endotoxin to the factor C, 22 μg/ml), and further, 10 μl of each fraction to make the total amount of 200 μl. After heating at 37° C. for 10 minutes, 20 μl of 0.005M Boc-Leu-Gly-Arg-pNA and 30 μl of a proclotting enzyme (0.96 mg/ml) was added to the mixture and further heated at 37° C. for 3 minutes. Then, 0.8 ml of 0.6M acetic acid was added thereto to stop the reaction and, the absorbance at 405 nm was measured.

After 40 ml of the factor C solution purified as described above was concentrated to 10 ml and 0.23 g of EDTA-4Na was added thereto for inhibiting the activation of factor C. To 1.0 ml of the resulting mixture was added the same amount of Freund's complete adjuvant. 0.3 ml, 0.3 ml and 0.4 ml of the same were subcutaneously injected (sensitization), respectively, into the back, the hip and the side of the abdomen of a rabbit (JW, ♂ 2.5 kg). The sensitization was effected 5 times in all at the rate of once per two weeks. One week after the final sensitization, the increase in the antibody titer was confirmed by means of the double immunodiffusion, and the cervical vein was cut to collect whole blood. Then, after allowing the obtained blood to stand at room temperature for 1 hour and further overnight at 4° C, the centrifugation was effected at 2,000 rpm for 5 minutes. 62 ml of the resulting serum was heat treated at 56° C for 30 minutes to inactivate the same followed by the addition of 0.06 g of sodium azide (0.1% (w/v)) as a preservative. To 48 ml of the resulting serum, 48 ml of a 34% (w/v) Na$_2$SO$_4$ solution was added and the formed precipitate was separated by centrifugation at 10,000 rpm for 30 minutes. The resulting precipitate was washed twice with a 17% (w/v) Na$_2$SO$_4$ solution, successively and dissolved in 50 ml of 0.1M Tris-HCl buffer (pH 8.0). Into the solution 7.5 g of solid Na$_2$SO$_4$ was dissolved with stirring, and the formed precipitate was dissolved in the above-described Tris-HCl buffer. This precipitation procedure was repeated three times at a Na$_2$SO$_4$ concentration of 7.5 g/50 ml. The final precipitate was dissolved in the above-described buffer and the resulting solution was passed through a Cellulofine GH-20m column equilibrated with 0.05M NH$_4$HCO$_3$ (2.8×90 cm, eluted with 0.05M NH$_4$HCO$_3$). The eluate was desalted, followed by freeze-drying to obtain the IgG solution of anti-factor C serum.

EXAMPLE 3

Production of monoclonal antibody to purified factor C 0.5 ml of the factor C (200 μg protein/ml) obtained in Example 2 was mixed with the same amount of Freund's complete adjuvant, and 0.2 ml and 0.3 ml of the same were subcutaneously injected into the back and the hip of a mice (BALB/C, 5 weeks old, body weight 25 g), respectively. The second sensitization was effected at two weeks later, and after three weeks, 0.3 ml of factor C (300 μg/ml) was intravenously injected to effect a final immunization. Four days after the final immunization, 9.3×10$^7$ spleen cells were separated and, then fused with 1.9×10$^7$ mice myeloma SP/O cells according to a conventional method to form hybridoma. It was confirmed that the obtained hybridoma can be bounded with factor C, or can neutralize factor C activity. Then, 0.2 ml of pristan (2,6,10,14-tetramethylpentadecane) was intraperitoneally injected into mice as described above, and one week after the injection, 3×10$^7$ hybridoma cells were intraperitoneally injected per animal. Two weeks thereafter, when a large quantity of ascites was accumulated, ascites was recovered and IgG fraction was precipitated with 40% saturated ammonium sulfate to finally obtain an ascites-derived monoclonal antibody.

EXAMPLE 4

Preparation of factor C-free lysate using anti-factor C antibody-fixed Cellulofine 100 ml of lysate obtained by the method described in Example 1 was applied to a column of anti-factor C antibody-fixed Cellulofine (its preparation is hereinafter described) (1.3×12 cm) containing no endotoxin and β-glucan, equilibrated with 0.1M Tris-HCl buffer (pH 8.0, containing 0.15M NaCl). After washing with 0.1M Tris-HCl buffer (pH 8.0 containing 1M NaCl), an unadsorbed fraction passed through the column was collected to obtain a lysate containing no factor C.

Preparation of anti-factor C antibody-fixed Cellulofine 10 g of formylcellulofine was thoroughly washed with 0.1M phosphate-Na buffer (pH 7.1), and was suspended in 10 ml of a solution of the anti-factor C antibody described in Examples 1 to 4 (10 mg/ml, 0.1M phosphate-Na buffer, pH 7.1), which was then dissolved by adding 50 mg of NaCNBH$_3$. The resulting solution was gently stirred at room temperature for 8 hours, and then washed with 0.2M Tris-HCl buffer (pH 7.0). After filtered, 5 ml of the above-described buffer containing 10 mg of NaCNBH$_3$ was added to the residue, followed by agitating at room temperature for 3 hours. Then, the resulting product was thoroughly washed with 0.1M Tris-HCl buffer (pH 8.0, containing 0.15M NaCl).

EXAMPLE 5

Determination of (1→3)-β-D-glucan using polyclonal antibody

Three kinds of reagents were prepared according to the following method, and the reactivities thereof to the following three samples were examined.

Reagent A was prepared by mixing 440 μl of the lysate, 440 μmol of magnesium chloride and 2.86 μmol of Boc-Leu-Gly-Arg-pNA, followed by freeze-drying. Reagent B was prepared by adding to the components of reagent A 220 μl of 0.02M Tris-HCl buffer (pH 8.0) containing the IgG fraction of anti-BC serum prepared in Example 1 (10 mg/ml), followed by mixing and freeze-drying. Reagent C was prepared by adding to the components of reagent A 220 μl of 0.02M Tris-HCl buffer containing the IgG fraction of anti-factor C serum prepared in Example 2 (10 mg/ml), followed by mixing and freeze-drying.

Each of three reagents was dissolved in 2.2 ml of 0.2M Tris-HCl buffer (pH 8.0), and 0.1 ml portions of the resulting solutions were poured into test tubes. Then, 0.1 ml of a sample was added thereto, and thoroughly mixed to effect a reaction at 37° C. for 30 minutes. After 30 minutes, to the reaction mixture were successively added 0.5 ml of 0.04% sodium nitrite in 0.48M hydrochloric acid, 0.3% ammonium sulfamate and 0.07% N-(1-naphthyl)ethylenediamine dihydrochloride so that pNA formed would develop color. Reactivities of the samples to the three reagents were determined by measuring an absorbance of the resulting solution at 545 nm. The results are shown in Table 1. From these results, it is apparent that the use of a reagent in which a polyclonal antibody to the fraction BC and a polyclonal antibody to factor C are added enables specific determination of (1→3)-β-D-glucan without suffering from any influence of endotoxin.

TABLE 1

| Sample (pg/tube) | | Reactivity (ΔA545 nm/30 min) | | |
|---|---|---|---|---|
| Glucan* | Endotoxin** | Reagent A no antibody | Reagent B factors B and C antibody | Reagent C factor C antibody |
|  | 2.5 | 0.455 | 0.001 | 0.001 |
| 3.0 |  | 0.231 | 0.233 | 0.230 |
| 3.0 | 2.5 | 0.688 | 0.234 | 0.233 |

*curdlan
**derived from E. coli 0111:B4

EXAMPLE 6

Determination of (1→3)-β-D-glucan

Two kinds of reagents were prepared according to the following method, and the reactivities thereof to endotoxin and (1→3)-β-D-glucan were examined. Reagent A was prepared by mixing 440 μl of the lysate, 440 μmol of magnesium chloride and 2.86 μmol of Boc-Leu-Gly-Arg-pNA, followed by freeze-drying. Reagent D was prepared by adding 100 μl of a solution of monoclonal antibody capable of neutralizing purified factor C prepared in Example 3 to the components of reagent A, followed by freeze-drying.

Each of two kinds of reagents was dissolved in 2.2 ml of 0.2M Tris-HCl buffer (pH 8.0), and 0.1 ml portions of the resulting solutions were poured into test tubes. Then, 0.1 ml of a sample was added thereto, and thoroughly mixed to effect a reaction at 37° C. for 30 minutes. After 30 minutes, to the reaction mixture were successively added 0.5 ml of 0.04% sodium nitrite in 0.48M hydrochloric acid, 0.3% ammonium sulfamate, 0.07% N-(1-naphthyl)ethylenediamine dihydrochloride so that pNA formed would develop color. Reactivities of the samples to the two reagents were determined by measuring an absorbance of the resulting solution at 545 nm.

Figure 2:
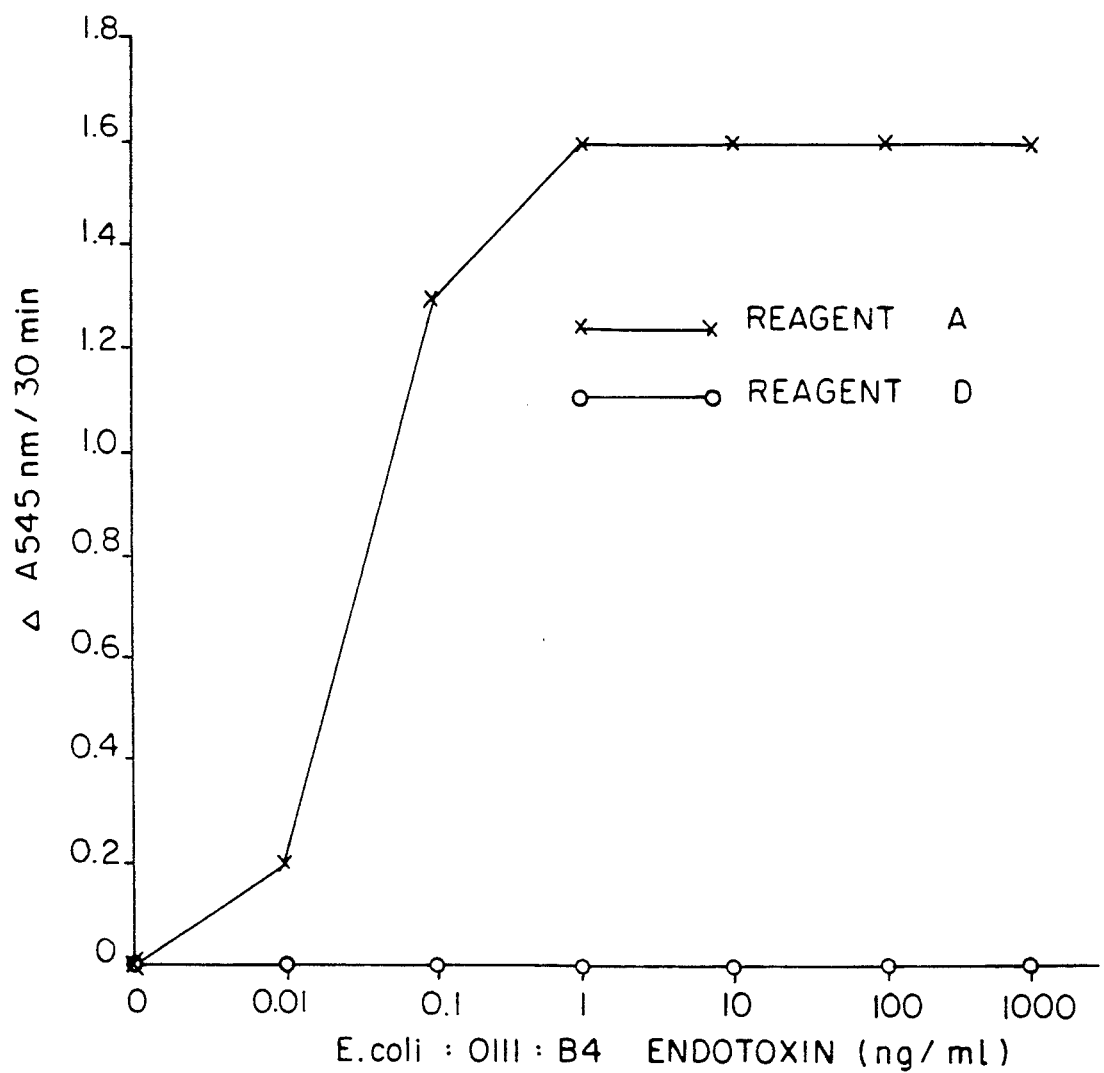
FIG. 2 shows reactivities of reagents A and D to endotoxin.

FIG. 2 shows the experimental results of comparison of reactivities of the reagents to endotoxin. Reagent A reacts with endotoxin depending upon a concentration. Reagent D, however, does not react even to 1,000 ng/ml of endotoxin at all. This result indicates that the monoclonal antibody to the purified factor C completely neutralizes factor C in the lysate so that factor C loses reactivity to endotoxin.

Figure 3:
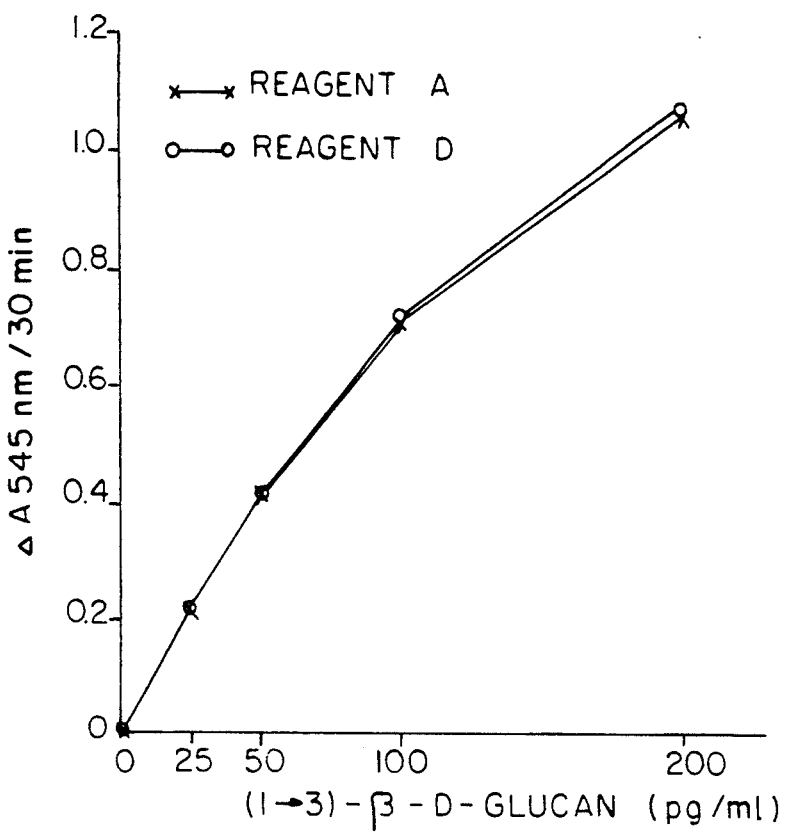
FIG. 3 shows reactivites of reagents A and D to $(1\rightarrow3)$-$\beta$-D-glucan.

FIG. 3 shows the results of comparison of reactivities of reagents A and D to (1→3)-β-D-glucan by means of a dosage reaction curve. The dosage reaction curves of these two reagents are substantially identical with each other, which indicates that the monoclonal antibody to the purified factor C included in reagent D does not affect the reactivity of the lysate to (1→3)-β-D-glucan at all.

Figure 4:
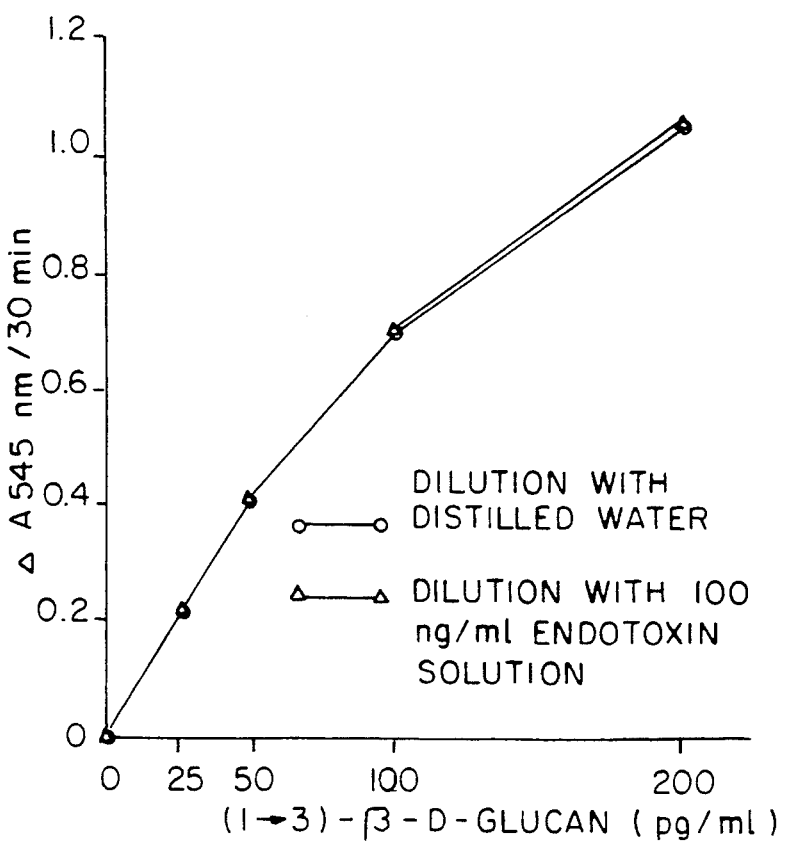
FIG. 4 shows reactivities of reagent D to $(1\rightarrow3)$-$\beta$-D-glucan diluted with water and endotoxin, respectively.

FIG. 4 shows the dosage reaction curves to dilution series of (1→3)-β-D-glucan with distilled water and with a 100 ng/ml of endotoxin solution. These two curves are substantially identical with each other, which indicates that the use of reagent D enables specific determination of (1→3)-β-D-glucan without suffering from any influence of endotoxin. From these results, it is apparent that (1→3)-β-D-glucan can be specifically determined by using a reagent containing the monoclonal antibody to the purified factor C without interference of endotoxin.

EXAMPLE 7

Determination of (1→3)-β-D-glucan

Two kinds of reagents were prepared according to the following method, and reactivities thereof to the following three samples were examined.

Reagent A was prepared by mixing 440 μl of the lysate, 440 μmol of magnesium chloride and 2.86 μmol of Boc-Leu-Gly-Arg-pNA, followed by freeze-drying. Reagent E was prepared by mixing 440 μl of the factor C-free lysate prepared in Example 4, 440 μmol of magnesium chloride and 2.86 μmol of Boc-Leu-Gly-Arg-pNA, followed by freeze-drying.

Each of two kinds of reagents was dissolved in 2.2 ml of 0.2M Tris-HCl buffer (pH 8.0), and 0.1 ml portions of the resulting solutions were poured into test tubes. Then, 0.1 ml of a sample was added thereto, and thoroughly mixed to effect a reaction at 37° C. for 30 minutes. After 30 minutes, to the reaction mixture were successively added 0.5 ml each of 0.04% sodium nitrite in 0.48M hydrochloric acid, 0.3% ammonium sulfamate and 0.07% N-(1-naphthyl)ethylenediamine dihydrochloride so that pNA formed would develop color. Reactivities of the samples to the two reagents were determined by measuring an absorbance of the resulting solution at 545 nm. The results were shown in Table 2. From these results, it is apparent that the use of a reagent containing the factor C-free lysate enables specific determination of (1→3)-β-D-glucan without any interference of endotoxin.

TABLE 2

| Sample (pg/tube) | | Reactivity (ΔA545 nm/30 min) | |
|---|---|---|---|
| Glucan* | Endotoxin** | Reagent A Lysate | Reagent E factor C-free lysate |
|  | 2.5 | 0.455 | 0.001 |
| 3.0 |  | 0.231 | 0.232 |
| 3.0 | 2.5 | 0.688 | 0.233 |

*curdlan
**derived from E. coli 0111:B4

EXAMPLE 8

Assay of a plasms specimen

Blood was aseptically collected from eleven patients hospitalized in blood department of Jichi Medical School, who suffered from grave hemopathy (acute lymphoblastic leukemia, acute myelogenous leukemia, multiple myeloma, etc.) and were doubted to be suffered from mycotic septicemia, heparin was added thereto to serve as a sample. The sample was centrifuged at 4° C., at 150×G for 10 minutes to obtain platelet-rich plasma (PRP). To 0.1 ml of the same was added 0.2 ml of 0.32M perchloric acid and the mixture was heated at 37° C. for 20 minutes. Thereafter, a deposit was removed by a centrifugation (3,000 rpm, 10 minutes). 0.05 ml of the supernatant was neutralized by adding 0.05 ml of 0.18M NaOH. This was used as a specimen.

Figure 5:
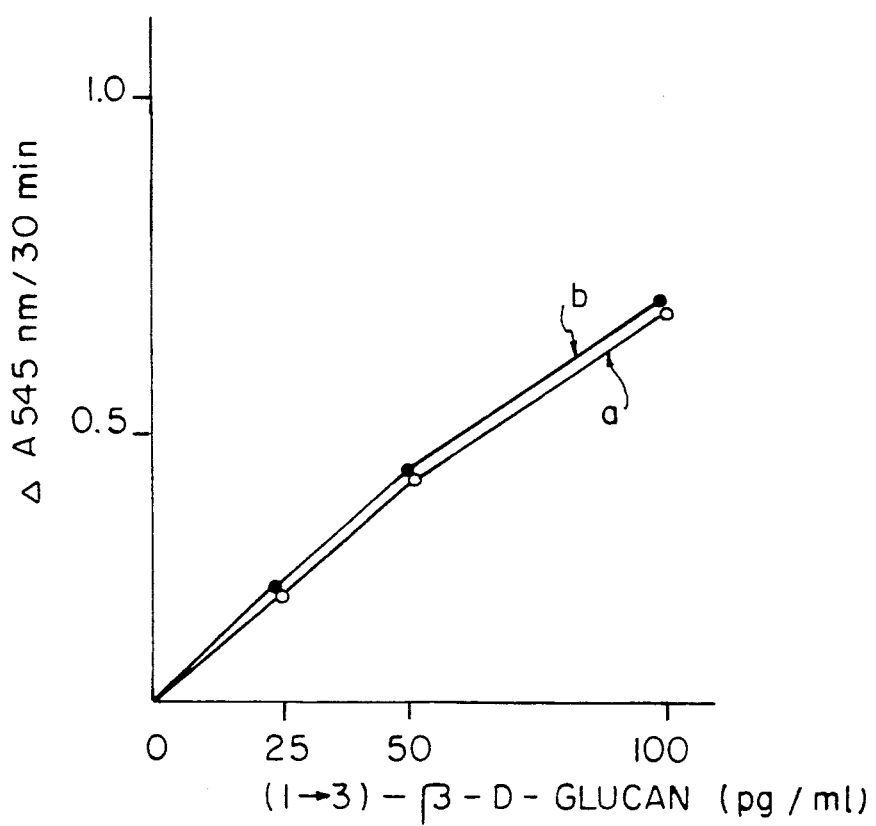
FIG. 5 shows calibration curves of $(1\rightarrow3)$-$\beta$-D-glucan of Examples 8 to 10.

Successively, 0.1 ml of the reagent for determining (1→3)-β-D-glucan according to the present invention prepared by the method described in Example 6 was added thereto, and the mixture was heated at 37° C. for 30 minutes. To the resulting solution, were successively added 0.5 ml each of 0.04% sodium nitrite in 0.48M hydrochloric acid, 0.3% ammonium sulfamate and 0.07% N-(1-naphthyl)ethylenediamine dihydrochloride to effect diazo-coupling. Then, an absorbance of the resulting solution was measured at 545 nm. The amount of (1→3)-β-D-glucan was shown by calibration curve a (FIG. 5) which was separately prepared. As shown in Table 3, a high concentration of (1→3)-β-D-glucan was detected in all of eleven cases (healthy subjects: 0.2±0.3 pg/ml). In five cases (No. 1 to No. 5) among them, *Candida albicans, Candida quilliermondii, Candida tropicalis, Candida krusei* and *Cryptococcus neoformans* were detected by blood agar culture. The other two cases (No. 6, No. 7) were negative by blood agar culture, but *Asperqillus fumiqatus* was detected by a tissue pathological examination in autopsy. Remaining four cases (No. 8 to No. 11) were negative by blood agar culture, though there could be little doubt of mycotic infection in view of, for example, clinical symptoms, progress and drug sensitivity. However, administration of antimycotic agents (amphotericin B, miconazole and fluconazole) resulted in remarkable improvements. Thus, it could be understood that the method according to the present invention is expected to be highly effective for a rapid diagnosis for mycosis, especially deep mycosis which is hardly detected by conventional test methods, except for examples of hemodialysis using a cellulose dialyzer (No. 1 to No. 5 in Table 4).

lowed by heating at 37° C. for 30 minutes. After diazo-coupling as in Example 8, an absorbance of the resulting solution was measured at 545 nm. The amount of (1→3)-β-D-glucan was calculated from calibration curve b (FIG. 5) which had been separately prepared. As shown in Table 5, a high concentration of (1→3)-β-D-glucan was detected (healthy subjects: 10 pg/ml or less) in all of three cases. Thus, it can be understood that the method of the present invention is expected to be highly effective for a rapid established diagnosis for mycotic urinary tract infectious diseases.

TABLE 5

| | (1→3)-β-D-glucan concentration in mycete-infected urine | | |
|---|---|---|---|
| No. | Detected mycete | CFU*/ml | (1→3)-β-D-glucan (ng/ml) |
| 1 | Candida albicans | >10⁴ | 25.5 |
| 2 | Candida albicans | >10⁴ | 13.0 |
| 3 | Candida glabrata | >10⁴ | 16.7 |

*Colony forming unit

EXAMPLE 10

Assay of cerebrospinal fluid specimen

Determination of (1→3)-β-D-glucan according to the method of the present invention was carried out with respect to patients who were doubted to suffer from

TABLE 3

| (1→3)-β-D-glucan concentration in plasma from patients suffered from opportunistic deep mycosis | | | | | | | |
|---|---|---|---|---|---|---|---|
| No. | Age/Sex | Disease | Granulocyte number | Plasma (1→3)-β-D-glucan | Blood agar culture | Remarks | Prognosis |
| 1 | 53/F | ALL | 0 μl | 304.6 pg/ml | (+) | Isolation of *Candida albicans* | Death |
| 2 | 72/F | MM | 960 | 402.0 | (+) | Isolation of *Candida guilliermondii* | Alive |
| 3 | 61/M | AML | 0 | 24.2 | (+) | Isolation of *Candida tropicalis* | Death |
| 4 | 45/M | APML | 0 | 87.6 | (+) | Isolation of *Candida krusei* | Alive |
| 5 | 59/M | AIHA | 2560 | 525.6 | (+) | Isolation of *Cryptococcus neoformans* | Alive |
| 6 | 48/F | ALL | 0 | 49.2 | (−) | Systemic Aspergillosis (autopsy) | Death |
| 7 | 65/F | APML | 0 | 145.1 | (−) | Systemic Aspergillosis (autopsy) | Death |
| 8 | 45/F | AML | 6278 | 645.6 | (−) | Improved by fluconazole | Alive |
| 9 | 52/M | ALL | 6 | 76.5 | (−) | Improved by miconazole | Alive |
| 10 | 32/M | AML | 1 | 39.0 | (−) | Improved by miconazole | Alive |
| 11 | 29/F | ALL | 0 | 264.4 | (−) | Improved by amphotericin B | Alive |

ALL: acute lymphoblastic leukemia.
AML: acute myelogenous leukemia.
APML: acute promyelocytic leukemia.
MM: multiple myeloma.
AIHA: autoimmune hemolytic anemia

TABLE 4

| (1→3)-β-D-glucan concentration in blood from patients whom hemodialysis with cellulose acetate dialyzer were applied | |
|---|---|
| No. | (1→3)-β-D-glucan (pg/ml) |
| 1 | 1528.0 |
| 2 | 2603.7 |
| 3 | 2051.5 |
| 4 | 1764.3 |
| 5 | 4028.0 |

EXAMPLE 9

Assay of urine specimen

Urinary (1→3)-β-D-glucan of three patients suffered from an urinary tract infectious disease complicated in the hospital of Jichi Medical School, from whom *Candida albicans* and *Candida glabrata* were detected by urinary culture, was determined according to the method of the present invention.

Intermediate urine was aseptically collected in a sterilized cup, and to 0.005 ml of the same, 0.2 ml of the reagent for determining (1→3)-β-D-glucan prepared according to the method described in Example 7, folmeningitis in the hospital of Jichi Medical School, and were confirmed to suffer from mycotic meningitis by detecting *Cryptococcus neoformans* in cerebrospinal fluid.

To 0.05 ml of cerebrospinal fluid aseptically collected by means of lumbar puncture, were added 0.05 ml of the reagent for determining (1→3)-β-D-glucan prepared according to the method of the present invention described in Example 5, followed by heating at 37° C. for 30 minutes. After diazo-coupling as in Example 8, an absorbance of the resulting solution was measured at 545 nm. The amount of (1→3)-β-D-glucan was calculated from the calibration curve b (FIG. 5) which has been separately prepared. As shown in Table 6, a high concentration of (1→3)-β-D-glucan was detected (healthy subjects: 1 pg/ml or less) in all of three cases. Thus, it can be understood that the method of the present invention is expected to be highly effective for an early rapid diagnosis for mycotic meningitis.

TABLE 6

| | (1→3)-β-D-glucan concentration in mycete-infected cerebrospinal fluid | |
|---|---|---|
| No. | Detected mycete | (1→3)-β-D-glucan (pg/ml) |
| 1 | Cryptococcus neoformans | 120.5 |
| 2 | Cryptococcus neoformans | 56.8 |
| 3 | Cryptococcus neoformans | 105.0 |

Industrial Applicability

As described above, the present invention provides a reagent for specifically determining (1→3)-β-D-glucan using lysate, which enables rapid, simple and accurate determination of mycotic (1→3)-β-D-glucan present in biological samples such as blood, urine and cerebrospinal fluid. Thus, this reagent is useful in a rapid diagnosis and evaluation of therapeutic effect of deep mycosis which is difficult to detect by means of conventional test methods represented by, for example, cultivation. Particularly, it greatly contributes to clinical diagnosis.

The present invention also makes it possible to rapidly and accurately determine (1→3)-β-D-glucan which contaminates distilled water for injection, medical supplies and injection drugs. Further, the present invention provides a means useful for screening anti-tumor polysaccharides represented by (1→3)-β-D-glucan. Thus, these secondary effects of the present invention greatly contribute to the field of the manufacture of drugs.

What is claimed is:

1. A method for determining (1→3)-β-D-glucan in a sample comprising the steps of:
   (a) admixing limulus amebocyte lysate and an antibody having binding specificity for endotoxin-sensitive factor, wherein said antibody neutralizes endotoxin-sensitive factor reactivity to endotoxin; and
   (b) contacting the resulting admixture with said sample, and assaying for clotting enzyme activity.

2. A method for determining (1→3)-β-D-glucan in a sample comprising the steps of:
   (a) removing endotoxin-sensitive factor from limulus amebocyte lysate by contacting the lysate with an antibody having binding specificity for endotoxin-sensitive factor, wherein said antibody is immobilized on a carrier; and
   (b) contacting the resulting endotoxin-sensitive factor-free limulus amebocyte lysate with said sample, and assaying for clotting enzyme activity.

3. A method for determining (1→3)-β-D-glucan in a sample comprising the steps of:
   (a) adding to a sample, an antibody having binding specificity for endotoxin-sensitive factor, wherein said antibody is capable of neutralizing endotoxin-sensitive factor reactivity to endotoxin; and
   (b) contacting the resulting mixture with limulus amebocyte lysate so as to neutralize endotoxin-sensitive factor reactivity to endotoxin, and assaying for clotting enzyme activity.

* * * * *